(12) United States Patent
Gillis

(10) Patent No.: US 6,340,590 B1
(45) Date of Patent: Jan. 22, 2002

(54) VERIFICATION OF THERMAL STERILIZATION

(75) Inventor: John R. Gillis, 10 Evergreen Dr. Suite E, Bozeman, MT (US) 59715

(73) Assignee: John R. Gillis, Bozeman, MT (US)

( * ) Notice: Subject to any disclaimer, the term of this patent is extended or adjusted under 35 U.S.C. 154(b) by 0 days.

(21) Appl. No.: 09/190,823

(22) Filed: Nov. 12, 1998

(51) Int. Cl.$^7$ ................................................ C12M 1/34
(52) U.S. Cl. ...................... 435/287.4; 435/31; 435/808; 422/58; 422/86
(58) Field of Search .................. 422/86, 58; 435/287.4, 435/808, 810, 31; 116/101, 206, 207, 216; 73/25.01

(56) References Cited

U.S. PATENT DOCUMENTS 4,311,793 A * 1/1982 Halleck .................... 435/287.4
4,353,990 A * 10/1982 Manske et al. .............. 435/287
5,418,167 A * 5/1995 Matner et al. .............. 435/288
5,529,931 A * 6/1996 Narayan ................... 435/287.4

\* cited by examiner

*Primary Examiner*—David A. Redding
(74) *Attorney, Agent, or Firm*—Shanley and Baker

(57) ABSTRACT

Thermal sterilization indicator process, apparatus and test indicator product which enable indication of microbial sterility achieved during a thermal sterilizer cycle by measuring visible light absorption due to chemical change in an encapsulated liquid indicator material, including measurements taken when a thermal sterilizer cycle is completed without a time delay requirement for spore growth, and in which the liquid indicator material includes a growth nutrient and microbes, so as to enable verification of achieved microbial sterility by measurement of the liquid indication subsequent to an incubation period following completion of the thermal sterilizer cycle.

11 Claims, 4 Drawing Sheets

VERIFICATION OF THERMAL STERILIZATION

INTRODUCTION

This invention relates to novel methods, apparatus and products for verification of the effectiveness of thermal sterilizing procedures. In particular, this invention is concerned with obtaining an indication of desired thermal sterilization which is available upon completion of a thermal sterilizing cycle free of any delay for incubating or measuring the growth of microbial organisms. A specific embodiment of the invention is concerned with a compatible indicator material for providing an indication of sterility upon completion of a cycle and, also, after an incubating delay period for growth of microbes so as to be capable of providing dual indication of the effectiveness of a thermal sterilizing cycle.

Commercial verification of thermal sterilization has been limited to evaluations after exposure to a thermal sterilizing cycle and after a predetermined period of incubation of a culture medium, to determine whether exposed microbes in the culture medium survived the thermal exposure. A predetermined period of incubation of two to about seven days under controlled conditions was necessary, after a sterilizing cycle was completed, for such microbial life testing.

Under those procedures, a sterilizer load was required to be quarantined until verification of sterilization was achieved through analysis of spore incubation procedures and results. Such delays cause difficulties for most laboratories, hospitals and similar institutions due to space limitations, supply inventories and time costs.

SUMMARY OF THE INVENTION

The present invention provides for elimination of such delayed verification testing for thermal sterilization results by enabling direct verification testing upon completion of a thermal sterilizing cycle, free of a requirement for an incubation period.

A load, comprising materials to be sterilized, is interspersed with test indicator ampoules containing a novel indicator material of the invention. Upon completion of a thermal sterilizing cycle, such indicator material enables direct verification of the effectiveness of the sterilizing cycle.

In carrying out such direct indication and verification procedures, a system is provided which measures a property of such novel indicator material, which is responsive to chemical change during thermal exposure in a sterilizing cycle; and, measurement of such property and verification of sterilization effectiveness are available directly upon completion of a thermal sterilizing cycle.

In a specific embodiment of the invention, the indicator material responsive to chemical change comprises a newly developed growth nutrient composition which not only enables direct verification of sterilizing effectiveness by such direct measurement of chemical change; but, also, enables verification of sterilizing effectiveness by providing for biological change following a spore incubation period.

The above and other advantages and contributions of the invention are considered in greater detail with references to the accompanying drawings.

DETAILED DESCRIPTION OF THE INVENTION

Figure 1:
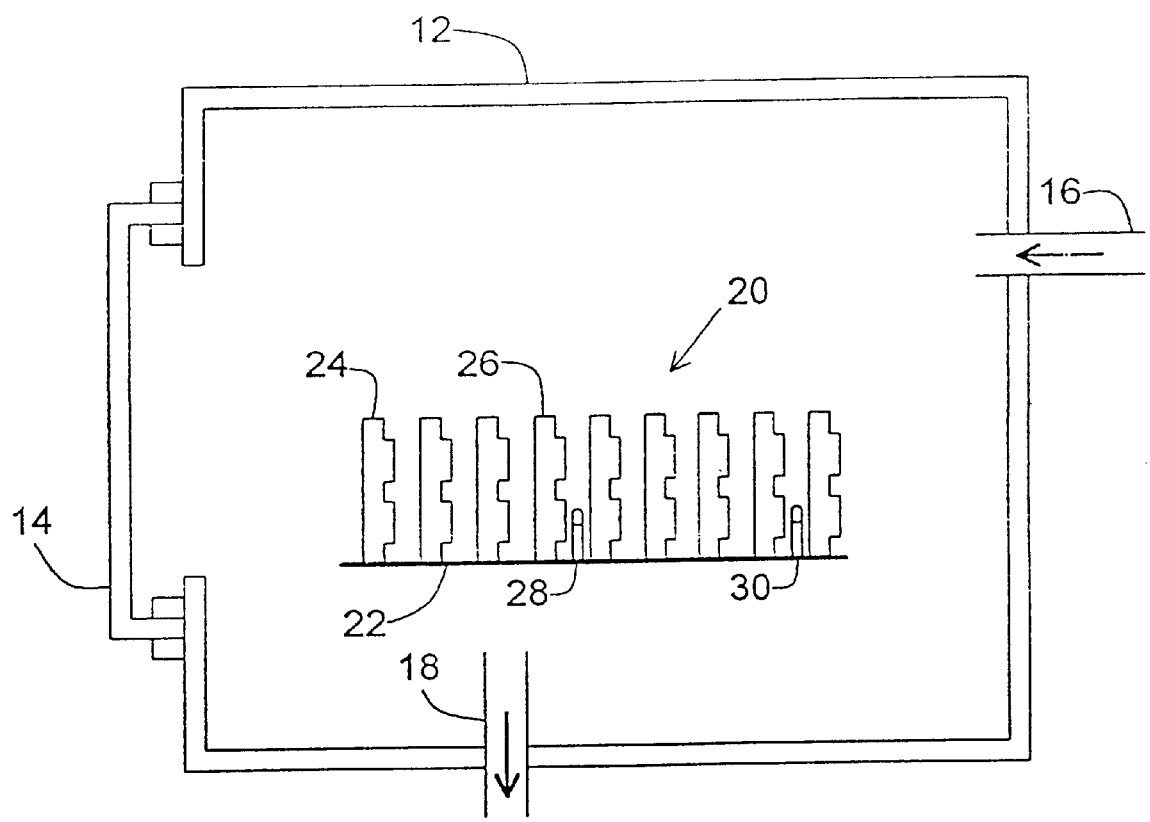
FIG. 1 is a schematic general arrangement elevational view, with portions cut away, of sterilizing apparatus for describing thermal sterilizing verification features of the invention.

In thermal sterilizer 12 of FIG. 1, door 14 defines and seals sterilizing chamber 15. An access 16 is used for introducing and replenishing a thermal sterilizing gas (typically referred as to steam herein), with exit 18 providing for controlled removal of spent steam.

Sterilizer load 20 is positioned within chamber 15 on shelving 22. Individual articles of the load, such as 24 and 26, are positioned to provide for circulation of sterilizing steam. Ampoules 28 and 30 of the invention are interspersed among the load for verifying effectiveness of sterilizing. Such ampoules for verifying sterilizing procedures are strategically placed, taking into account heat transfer principles, particularly in areas where circulation of sterilizing steam can be more difficult than in other areas. Such ampoules are distributed in sufficient numbers to obtain reliable assurance of desired thermal exposure throughout the load.

Prior biological indicators required an incubation period of about two to seven days following a thermal sterilizing cycle. After such incubation period, it was necessary to examine the test indicators to determine if microbial growth had occurred. If desired sterility was not achieved, a thermal sterilizing cycle had to be repeated following such delay.

With the present invention, verification of desired microbial kill is obtained directly upon completion of a sterilizing cycle by measurement of a property which is responsive to chemical change in an indicating material developed as part of the invention.

Such chemical-change property, analysis methods and measurement apparatus of the invention are described in more detail later herein. Also, a compatible indicator embodiment of the invention for directly indicating such chemical change, and capable of a biological verification, after a delay period, is described in more detail later.

Figure 2:
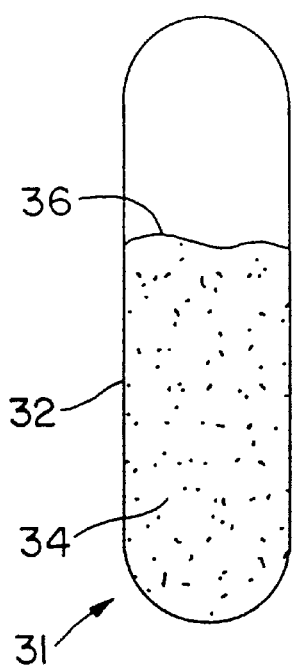
FIG. 2 is an enlarged view, in cross section, of an encapsulating embodiment for an indicator material which is capable of compatible uses.

FIG. 2 is a cross-sectional view of an encapsulated embodiment of the invention, referred to as an ampoule, for verifying effectiveness of a sterilizing cycle. Ampoule 31 includes an encapsulating barrier 32 which is impermeable to penetration of liquid, gas, or microbes from externally of the barrier. Such encapsulating barrier can be a polymer, such as polycarbonate or polypropylene, glass, or the like, which is permeable to light frequencies selected herein and which is structurally and physically capable of withstanding exposure to a thermal sterilizing cycle.

In a compatible ampoule embodiment made possible by present teachings, microbes 34 are enclosed within ampoule 31; and, as shown, are suspended in a liquid or gel indicator material 36 developed as part of the invention. In a preferred embodiment, the indicator material of the invention comprises a new composition growth nutrient. In FIG. 2, spores are associated with that growth nutrient, the composition of which is described more specifically later herein. Such new composition is capable of supporting growth of surviving microbes, such as *Bacillus stearothermophilus* spores and/or *Bacillus subtilis* spores.

Figure 3:
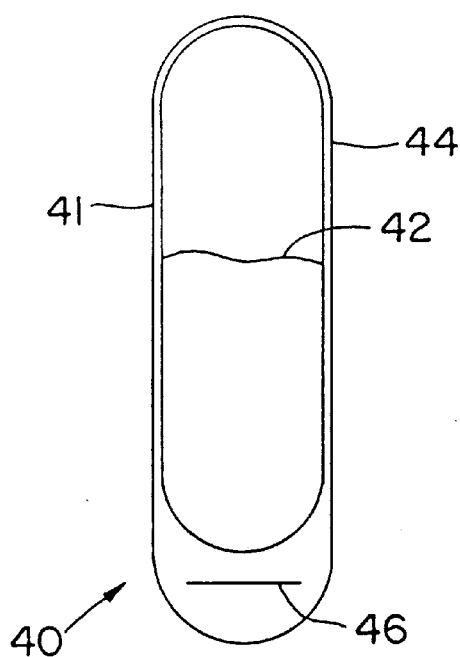
FIG. 3 is an enlarged view, in cross section, of an additional encapsulating embodiment of an indicator material of the invention capable of compatible uses.

In another encapsulating ampoule 40 of the invention, which is schematically depicted in cross section in FIG. 3, microbes are positioned within an outer capsule barrier but in a position so as to be capable of being associated with the new composition of the invention. An inner capsule barrier 41 is impermeable to liquid, gas, and microbes, and contains indicator material 42; no microbes are present within inner capsule barrier 41. Outer capsule barrier 44 of ampoule 40 is impermeable to liquid and microbes, but permeable to gas, and it encapsulates inner capsule barrier 41. A source of microbial life 46, such as filter paper which is laden with bacteria, is located within outer barrier 44 but exterior to inner barrier 41.

In addition to the above-mentioned properties, outer capsule barrier 44 of ampoule 40 is selected to be flexible while inner capsule barrier 41 is selected to be breakable. By applying pressure to deform outer barrier 44, inner barrier 41 is broken without breaking outer barrier 44. Growth nutrient indicator material 42, from within capsule barrier 41, is released and associated with the microbes on filter paper 46; that association is carried out after other procedures of the invention and is selectively coordinated with the start of an incubation period.

In the ampoules of FIGS. 2 and 3, a pH indicator ingredient (as later described), or other ingredient, is enclosed for purposes of achieving a biological-change verification of sterilizing effectiveness.

Figure 4:
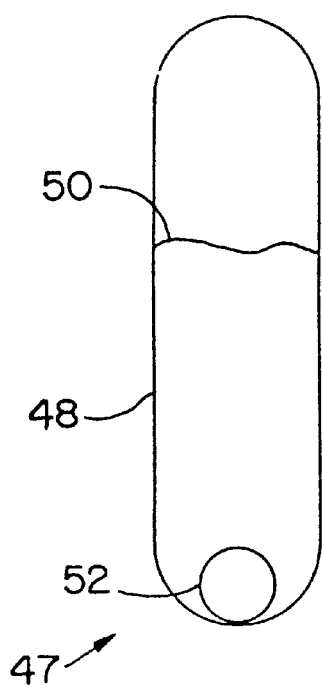
FIG. 4 is an enlarged view, partially in cross section, of a further encapsulating embodiment of the indicator material of the invention for correlating chemical-change measurements.

A further ampoule embodiment 47 of FIG. 4 is free of microbes or such biological measuring ingredient. Capsule barrier 48 is impermeable to gas, liquids and minerals but is permeable to selected visible light wave frequencies. The new-composition indicator material 50 is the same as that of the basic composition of the indicator material of FIG. 2 (or FIG. 3), but is free of microbes and the biological measuring ingredient forming part of the compatible material 36 (or the mix of FIG. 3, after breaking inner vial 44).

Bead 52, within outer capsule barrier 46, is provided for quick and easy identification of the ampoule 47 of FIG. 4. Ampoule 47 has been devised to assist in correlating and verifying chemical change values of that phase of sterilizing verification indicator system of the invention forming part of a specific compatible embodiment of the invention.

A quantitatively measurable property which is responsive to chemical change in the indicator material, which chemical change is responsive to thermal exposure during a cycle, has been selected. In a preferred embodiment, that property enables quantitative measurements of color change to be made based on absorbance of visible light of selected frequencies. Therefore, for each ampoule of FIGS. 2, 3 and 4, the capsule barriers are selected to be transparent to selected visible light wave frequencies so that a color change, responsive to chemical change of the indicator material, can be accurately analyzed in accordance with the invention.

Also, a predetermined-composition growth nutrient has been developed, as part of the invention, which changes color responsive to the chemical change caused by such thermal exposure. That new-composition growth nutrient can also be later used for verification of sterilization effectiveness of a cycle by providing for biological verification of surviving microbes, if any. A compatible indicator material, with a quantitatively measurable property responsive to chemical change, which is promptly indicative of effectiveness of a thermal sterilizing cycle; and which, in addition, enables a biological verification of thermal sterilizing effectiveness provides a significant endorsement for the invention which will contribute to worthwhile practical usage of the invention.

The composition of that newly developed sterility indicator material was selected so as to provide carbohydrates, and associated ingredients, which produce a quantitatively measurable color change correlated to chemical change, which chemical change is correlated to thermal exposure during a thermal sterilizing cycle. And such new composition was constituted as a compatible growth nutrient for measuring biological change. Other parameters bearing on finding constituents for the newly developed indicator material are considered later herein.

An objective, for compatibility proposes, was to produce an indicator material capable of quantitative measurement of chemical change; also, the combined constituents must not be deleteriously affected by the presence of microbes or a pH change ingredient. As taught herein, the constituents of a growth medium indicator material are selected to provide correlation between a property change, which is quantitatively measurable optically, and to provide effectiveness in maintaining capability for supporting any surviving microbes when incubated, while not interfering with quantitative measurement of color change.

Sterilizing temperature s) and time(s) are selected to quantify thermal exposure. A compatible indicator material has been developed which responds quantitatively to thermal exposure to provide a measurable property which can be correlated with microbial kill and sterility of the load. In a specific embodiment, a chemical-change caramelization of carbohydrates in the indicator material provides a quantitatively measurable color change which is correlated with chemical change due to thermal exposure, and is indicative of effectiveness of the thermal sterilizing cycle.

For compatible-type sterility test ampoules of the invention, the biological change ingredient is chosen to have a melting point and decomposition temperature significantly higher than the range of temperatures employed in a thermal sterilizer. Bromcresol purple is preferred for pH indication and produces a color change from purple to yellow with microbial growth. Further, it does not interfere with quantitative measurements of color change, due to chemical change, which are made without requirement for an incubation period following the sterilizing cycle. A quantitatively measurable color change, due to caramelization of the carbohydrate-based composition described above, is thus available upon completion of a thermal sterilizing cycle; and, that color change measurement is unaffected by the presence of microbes or a pH ingredient for later biological-change measurement.

By proportioning carbohydrate concentration, the degree of caramelization, and the associated color change due to that chemical change, are made quantitatively proportional to microbial kill in a thermal sterilizing cycle, so as to enable verification of the effectiveness of a thermal sterilizing cycle upon completion of the cycle; such indication is available free of delay requirement for microbial growth, and without a requirement for quarantine of a load during an incubation period.

The composition of the indicator material for the specific embodiment of a compatible-use ampoule of the invention has been selected to provide responsive color change resulting from the caramelization chemical change during thermal exposure and to correlated with percentage microbial kill. Further, such color change has been established to be linearly responsive to exposure time at a fixed sterilization temperature.

Apparatus of the invention for such quantitative measurement sterilizing effectiveness is based on analysis of such color change in indicator material within a sterility test ampoule. In a specific embodiment, quantitative measurements rely on absorbance of a selected visible light frequency to accurately measure color change, due to such chemical change, and data is identified at selected sterilizing temperatures and exposure times. Such quantitative optical measurements are made at a standard ambient temperature, selected at about 20° C. (about 68° F.).

Figure 5:
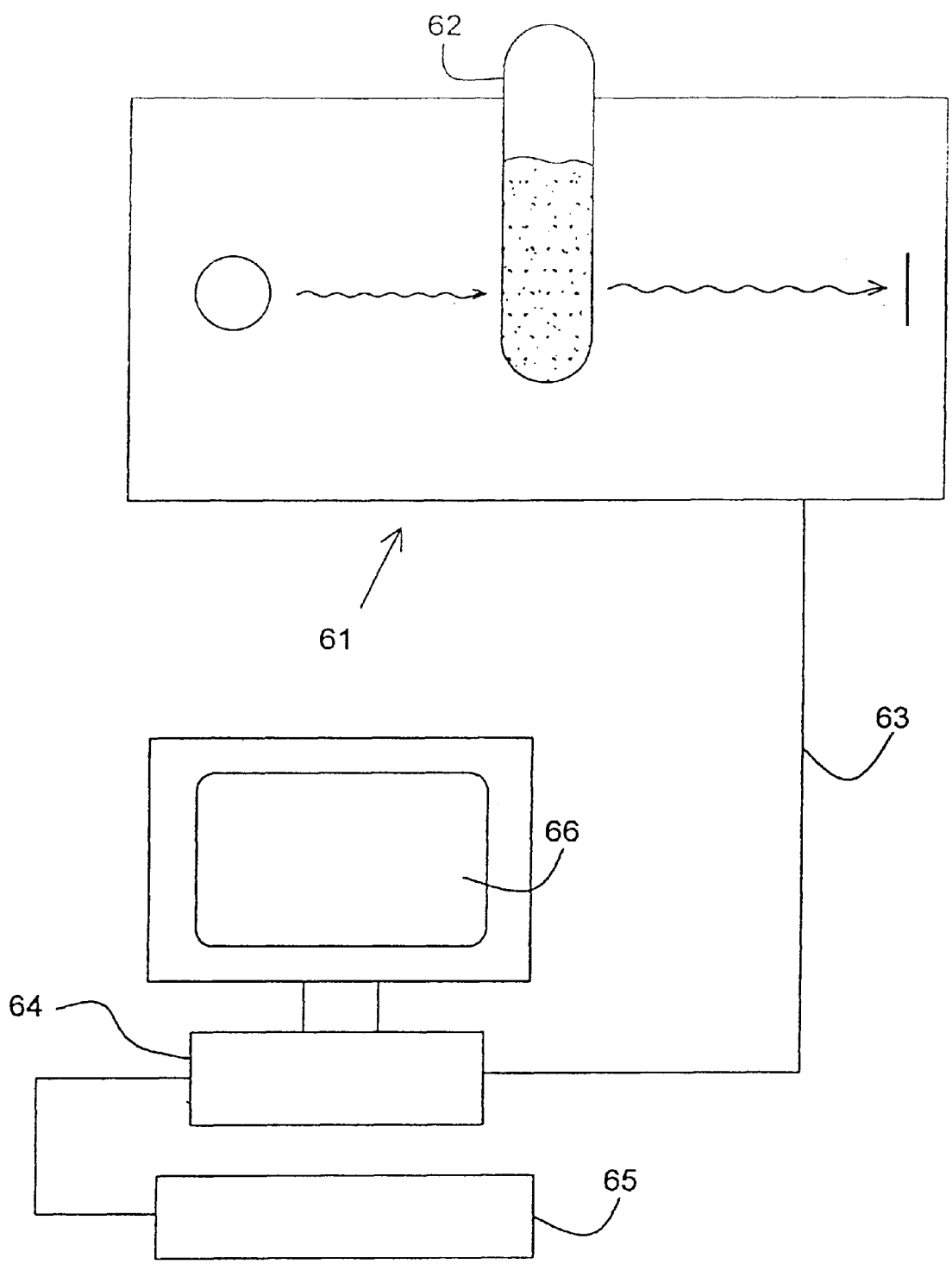
FIG. 5 is a schematic presentation, partially in cross section, of a specific embodiment of apparatus for describing analyzing procedures of the invention.

Visible light spectral analysis for color change of exposed ampoules of the invention has been selected for accuracy, ease of operation of combined components of the apparatus, and for reasons of economy. FIG. 5 depicts a specific embodiment of a rapid indicator system in which spectrophotometer measurements, and other data, are combined using microprocessor equipment, such as a digital computer. Spectrophotometer 61 measures selected wavelength light absorbance by caramelized indicator material of test ampoule 62 (FIG. 3), which has been exposed to a thermal sterilizing cycle. The system of FIG. 5 can be used in analysis of ampoules of the type described in relation to FIGS. 2, 3 or 4. In practice, ampoules of the type shown in FIG. 2 and 3 are used for compatible-type verifications; that is, in which biological change indication is made optionally available for verification of the chemical change indication.

The ampoule of FIG. 4 was developed to test the newly developed compatible color-change indicator material with or without microbial spores and an ingredient which is color-coded to pH change. Also, for assurance that any change in color of an indicator material, after incubation, due to spores and a pH biological color change indicator, is readily discernable.

In FIG. 5, absorbance readings of selected wavelengths by spectrophotometer 61 are directed electronically through connector 63 for processing by digital computer 64. Absorbance readings, as measured at selected frequencies by the spectrophotometer, can be stored for processing in the digital computer. Data, such as sterilization temperatures, sterilizing test indicator identification, information such as minimum values relating to sterility, product and other identification information, are introduced manually through input keyboard 65. System software enables carrying out statistical functions and ratio calculations, as well as graphic display on video 66 and printout capability.

A preferred method for obtaining quantitative optical measurements of a color-change property involves measuring absorbance readings at more than one visible light wavelength. As taught herein, absorbance readings of an indicator material are measured at two separate light wavelengths, one of which is the peak height of absorbance at a frequency not responsive to the thermal conditions encountered; and the remaining of which is the peak height of absorbance at a frequency which is responsive to the thermal conditions encountered. A ratio is calculated based on those two absorbance readings. Such optical property result, calculated as the ratio of those two absorbance readings, accurately indicates microbial kill and is defined as the Lethality Index (LI) value.

In calculating an LI value, an absorbance reading of the ampoule indicator material is measured at a standard wavelength ($A_{STD}$) and at a reference wavelength ($A_{REF}$). The LI value is calculated as the ratio of $A_{STD}$ to $A_{REF}$. Such method of obtaining an LI value is utilized so as to minimize factors that could otherwise negatively affect the accuracy of measurements of absorbance readings. One such factor could be the absorbance of light by an encapsulating barrier for an ampoule being analyzed which takes into consideration that such absorbance could vary when ampoules are manufactured from different barrier materials; and could, therefore, detract from precise measurement of color change in the indicator material. Elimination of such factors increases reliability of LI values calculated as described above.

A standard absorbance reading at 325 nm and a reference absorbance reading at 590 nm have been found to produce reliable LI values in measuring the newly-developed indicator material color change responsive to chemical change. The reliability of such wavelengths was verified by use with constituents developed for the growth indicator material of the invention; namely: tryptone, glucose, soytone, soluble starch and yeast extract. Absorbance readings were measured for each such constituent throughout an absorbance spectrum of 325 nm to 590 nm. Such absorbance spectrum data were measured for each constituent prior to sterilization, at $t_o$, as well as after a sterilizing cycle of $t_s$=30 minutes at 121° C.

A strong absorbance was measured for all growth medium constituents at 325 nm at times $t_o$ and $t_s$; however, a significant change was found in absorbance values at to and $t_s$. Additionally, it was established that there was a very weak absorbance by the growth medium constituents at 590 nm; and that only a negligible change in absorbance readings for each occurred between $t_o$ and $t_s$. Thus, an absorbance reading at 325 nm provides an absorbance value corresponding to color change of the compatible indicator material of the invention, so that 325 nm is the preferred standard wavelength. The preferred reference wavelength is 590 nm because an absorbance reading, at such wavelength, provides a value that most effectively eliminates extraneous factors from the LI value.

The above rapid verification system data processor embodiment verifies sterility based on analysis of quantitative measurements of an optical property of the indicator material which is responsive to the chemical change, such as caramelization, during exposure time within a thermal sterilizer. Such verification is based on a predetermined correlation between indicator color and percentage of microbial kill (or survival) at a selected sterilization temperature. Further, a method has been devised to establish a minimum optical property quantitative measurement value, from such correlated data, which can provide a minimum threshold at which indicator material color change verifies sterility. Such a minimum optical property quantitative measurement value is preferably established at a selected sterilization temperature which corresponds to 100% microbial kill at a designated minimum exposure time.

Establishing a minimum optical property quantitative measurement value for a selected sterilization temperature was accomplished by performing a series of sterilizing cycles at such temperature in which sterilization test indicators are of the type described in FIG. 2 or FIG. 3. Such thermal sterilizing cycles yield necessary correlated data for establishing the minimum optical property quantitative measurement value for a fixed sterilizing temperature. Each sterilizing cycle is carried out with a set of indicators and at a selected exposure time. Quantitative optical property measurements are obtained for each set of indicators as each sterilizing cycle has been completed. The derived correlated data are produced by relating optical property quantitative measurements and varying exposure times as stored for analysis and processing in the rapid indicator system data processor described above.

Indicator ampoules were then incubated for a sufficient period of time to determine if there were any microbial survival in any of the example indicators. After such incubation period is complete, a minimum optical property measurement values can be determined. Such minimum optical property quantitative measurement value represents the average quantitative measurement for such set of indicators that corresponds to 100% microbial kill and verifies the minimum exposure time for correlated verification by measurement of chemical change in the indicator material, as a sterilizing cycle is completed, free of an incubation period delay.

Incubation procedures, for compatible-use ampoules of the invention, involve storing indicator ampoules in a temperature-controlled environment, preferably between 50° C. and 60° C., for a period of up to about seven days. Incubation is carried out to determine whether any microbial growth occurs in the indicators after completion of a thermal sterilizing cycle. When indicators such as depicted in FIG. 3 are used, the culture medium containing inner barrier is broken as previously described.

Observation of any pH color change in the compatible indicator ampoules, over a period of from one to seven days, indicates whether required sterility was obtained by the thermal sterilizing cycle; and verifies the color-change indication of sterility.

The ampoule of FIG. 4 provides assurance for the chemical-change sterility indication by providing a reference for the degree of color change in the indicator material due to chemical change. During a sterilizing cycle, any color change in the indicator material of the ampoule of FIG. 4 results solely from caramelization which can provide a control reference for assurance verification for ampoules (FIG. 2 or 3), exposed in the same cycle in which indicator material contains microbes and a pH ingredient. It has been established that, following the thermal sterilizing cycle and prior to incubation, the color of the indicator material within each such ampoule type will remain the same. The color of the FIG. 4 assurance indicator material will not change following an incubation period because no microbes are present. Therefore, a comparison of the color of the FIG. 2 or 3 ampoule type, following incubation, provides a readily observable visual detection as to whether or not a color change has occurred; a change of color indicates microbial growth in a microbe-laden ampoule.

A test ampoule of the invention contains about 1,000,000 spores of *Bacillus stearothermophilus*, suspended in from about 0.30 ml to about 0.45 ml of an aqueous indicator material of the invention, which contains the following constituents:

| Constituent | Concentration (Grams/Liter) |
| --- | --- |
| Tryptone | 8.5 |
| Glucose | 5.0 |
| Soytone | 1.5 |
| Yeast Extract | 0.5 |

-continued

| Constituent | Concentration (Grams/Liter) |
| --- | --- |
| Soluble Starch | 1.0 |
| Bromcresol Purple | 0.0024 |

Figure 6:
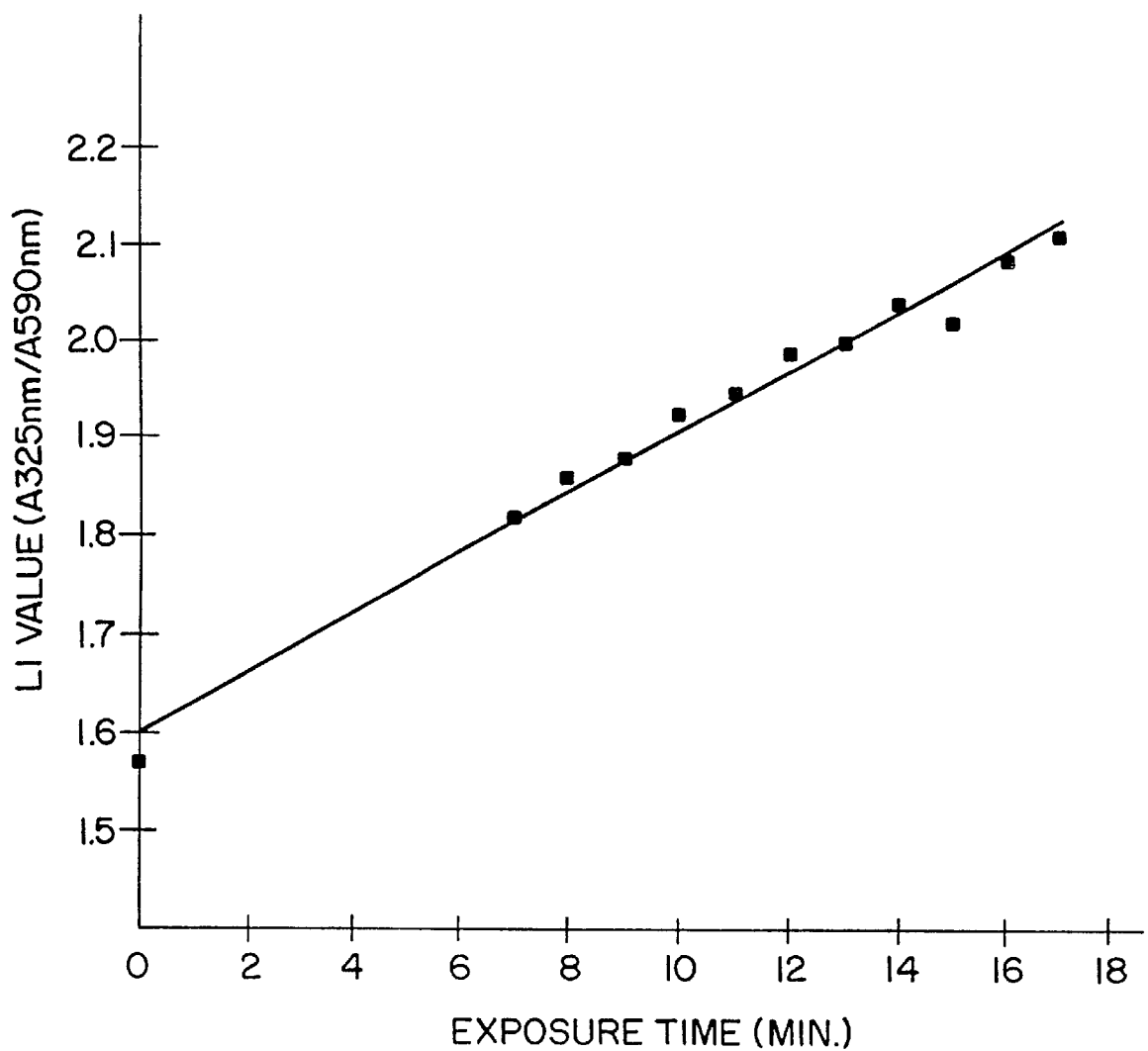
FIG. 6 is a graphical presentation of data resulting from practice of the invention utilizing analyzing procedures such as described in relation to FIG. 5.

Spectrophotometric measurements were carried out by placing the ampoules in a specially designed spectrophotometer which measured absorbance values at 325 nm and 590 nm and the absorbance values for each indicator which were converted to LI values (as described above). The data verified a substantially linear relationship between LI values and exposure times at a selected sterilization temperature. This linear relationship has been found to exist substantially throughout the temperature ranges and time periods associated with thermal sterilizing cycles, as can be seen in FIG. 6. The linear correlation coefficient for the data represented in FIG. 6 is $R^2=0.9846$.

After analyzing the test indicators spectrophotometrically, the indicators were incubated for at least 2 days at 57° C. and then examined for microbial growth. The incubation results are provided in Table II.

TABLE II

Survival/Kill Results After Incubation, 121° C.

| Exposure Time (Minutes) | Percentage of Indicators Having Living Microbes (Incubation Results) | LI (mean) |
| --- | --- | --- |
| 0 | 100% | 1.568 |
| 7 | 100% | 1.818 |
| 8 | 100% | 1.862 |
| 9 | 100% | 1.879 |
| 10 | 100% | 1.926 |
| 11 | 40% | 1.946 |
| 12 | 20% | 1.987 |
| 13 | 0% | 2.004 |
| 14 | 0% | 2.040 |
| 15 | 0% | 2.022 |
| 16 | 0% | 2.088 |
| 17 | 0% | 2.114 |

As indicated by Table II, an increase in LI corresponds to a decrease in living microbes within the indicators. An exposure time of 10 minutes at 121° C. for a tested lot resulted in all indicators testing positive for survival of microbes. However, a total kill of all microbes in all test indicators was confirmed after 13 minutes. The corresponding LI value for such confirmed total kill was LI=2.004. Such value is the minimum optical property (LI) value for that lot of sterilization test indicators subjected to a 121° C. sterilizing cycle.

Thus, in sterilizing cycles at 121° C., an LI value corresponding to biological-change verification in a load can be determined immediately after sterilization. If such LI value is 2.004 or greater, sterilization of the load is verified. An LI value of less than 2.004 would indicate less effective sterilizing results.

Such development data verify that the color change due to chemical change in indicator material of a test ampoule subjected to a fixed sterilization temperature, as quantitatively measured, provides a correlated indication of sterility which is available upon completion of a thermal sterilizing cycle, free of a requirement for an incubation period and measurement of biological change.

The rapid indication of sterility made available by such chemical change verification allows significant improvements in efficiency and use of thermal sterilizing cycles. For example, in production-line processing where subsequent steps, such as packaging, were previously delayed until biological-change indication of successful sterilization was available. With the rapid indication of the present invention, such delay and quarantine periods can be eliminated.

While specific indicator materials, bacteria, ampoule structures and configurations, absorbance measuring equipment, analytical wavelengths, and other specific values have been set forth during description of the invention, those skilled in the art recognize that modifications in such specific values can be determined, in the light of the above teachings, while relying on basic precepts and principles of the invention. Therefore, for purposes of determining the scope of the present invention, reference shall be made to the appended claims.

What is claimed is:

1. A system for indication of microbial sterility of a thermal sterilizer load, upon completion of a thermal sterilizing cycle, including
    sterility test ampoule means in which individual test ampoules are interspersed among articles of such a load to be sterilized, with:
        such ampoule means being capable of withstanding thermal exposure of such a thermal sterilizer cycle, concurrently with such load, each such ampoule comprising
    a sealed encapsulating exterior barrier, which:
        (i) is impermeable to penetration by liquid, gas, or microbes from externally of such encapsulating barrier,
        (ii) transmits radiation in the visible light spectrum, and
        (iii) seals a liquid indicator material containing a preselected carbohydrate in solution, which:
            (a) provides a quantitatively-measurable visible change responsive to chemical change in such indicator material resulting from thermal exposure in such thermal sterilizer during such a thermal sterilizer cycle, so as to
            (b) correlate temperature, resulting from such thermal exposure and microbial kill within such a sterilizer load,
    such measurable visible chemical change in such indicator material being available directly as such a thermal sterilizer cycle is completed, free of a requirement for a time delay period for microbial growth in order to obtain an indication of microbial sterility.

2. The system of claim 1, in which such liquid indicator material comprises
    a growth nutrient for spores, and contains
        (i) microbial spores, and
        (ii) a pH indicator responsive to spore growth, so as to be further capable of providing:
            a biological-change verification of microbial sterility which is available. after a preselected incubation period which follows completion of such thermal sterilizer cycle.

3. The system of claim 2, in which
    positioning of such microbial spores, within such sealed encapsulating exterior barrier of such an ampoule, is selected from the group consisting of:
        (a) combined with such growth-nutrient liquid indicator material, and
        (b) capable of being combined with such indicator material while maintaining such sealed encapsulating exterior barrier.

4. The system of claim 3, further including
    means for quantitative measurement of such visible change property which is responsive to chemical change of such indicator material resulting from thermal exposure of such sterilizer cycle, and
    means for analyzing such measurement which is responsive to chemical change so as to quantify microbial sterility of such cycle.

5. A system for analyzing and verifying microbial sterility of a thermal sterilizer load, after scheduled exposure at a preselected sterilization temperature for a preselected exposure time, including
    sterility test ampoule means, with individual ampoules being capable of being interspersed among articles of such a load to be sterilized, which are
    capable of withstanding thermal exposure concurrently with such thermal sterilizer load, with
        an individual test ampoule comprising
            a sealed encapsulating exterior barrier which is impermeable to penetration of liquid, gas or microbes from externally of such barrier,
    such encapsulating barrier sealing
        (i) a liquid sterility indicator material, which functions to provide:
            a quantitatively measurable color-change responsive to chemical change within such indicator material, which
            correlates such scheduled thermal exposure, and microbial sterility resulting from thermal exposure achieved during such sterilizer cycle, which is available directly as such scheduled thermal exposure is completed, free of any time delay requirement for microbial growth, with such liquid indicator material including
        (ii) a growth-nutrient for spores, and
        (iii) microbial spores, so as to further provide:
            a biological-change indication of microbial sterility which is available after a preselected time delay period for microbial growth, subsequent to completion of such scheduled thermal sterilizer cycle; with
    such system further including:
        (a) measuring means for quantitative measurement of such color-change property upon completion of such thermal sterilizer cycle, and
        (b) measuring means for quantitative measurement of such indicator material, following such delay for microbial growth after completion of such scheduled thermal cycle, so as to quantify any biological change in such indicator material due to spore growth to verify such color-change indication of microbial sterility.

6. A sterility test ampoule for indicating. sterilization effectiveness directly as a thermal sterilizer cycle is completed, comprising
    a sealed encapsulating exterior barrier which transmits radiation in the visible light spectrum, while being impermeable to penetration of microbes from externally of such barrier, and which contains:
        a liquid indicator material which provides for quantitative measurement of visible change resulting from chemical change in such indicator material which is responsive to thermal exposure provided by such a thermal sterilizer cycle,
        such quantitative measurement of such visible change enabling a direct indication of sterilization effectiveness available upon completion of thermal sterilizer cycle, which indication is free of a time delay requirement for spore incubation.

7. The test ampoule of claim 6, in which such liquid indicator material sealed within such encapsulating barrier, includes:
   (A) a preselected carbohydrate growth nutrient for microbes;
   (B) a pH indicator ingredient which is responsive to microbial growth; and
   (C) microbial spores with positioning of such spores being selected from the group consisting of:
      (i) combined with such growth nutrient in such liquid indicator material within such encapsulating barrier, and
      (ii) capable of being combined with such growth nutrient in such liquid indicator material within such encapsulating barrier, without disturbing such sealed exterior barrier to penetration of liquid, gas or microbes from externally thereof;
   (D) such pH indicator ingredient being responsive to growth of any remaining microbial spores in such liquid indicator material following completion of such sterilizing cycle, so as to enable use of such test ampoule, by selection from the group consisting of:
      (i) chemical-change color indication of sterilization effectiveness directly as such a thermal sterilizing cycle is complete, free of any time delay requirement for spore growth,
      (ii) biological-change indication of sterilization effectiveness as a result of growth of microbial life in such liquid indicator material, after a growth period delay following completion of such cycle, and
      (iii) a combination of (i) and (ii).

8. The test ampoule of claim 7, in which
   such encapsulating barrier is substantially transparent to radiation within the visible light spectrum, and in which
   growth-nutrient in such indicator material produces a color change responsive to thermal exposure, which color change provides a direct indication of sterilization effectiveness by absorbing radiation of at least one wavelength selected within such visible light spectrum.

9. Method for verification of thermal sterilization of a sterilizer load, upon completion of a thermal sterilizer cycle, including:
   (A) providing sterilization test ampoule means, as set forth in claim 7, with a plurality of individual test ampoules capable of being interspersed selectively among articles of a sterilizer load for such thermal sterilizer cycle;
   (B) providing means for measuring such chemical change within such indicator material due to exposure to such thermal sterilizer cycle;
   (C) measuring such chemical change in such indicator material within such sealed encapsulating barrier so as to establish an indication of sterilization effectiveness upon completion of such sterilizer cycle;
   (D) providing for a time delay for spore growth within a predetermined number of such individual test ampoules upon completion of such thermal sterilizer cycle; and
   (E) providing for verification of microbial sterility responsive to temperature exposure achieved by such sterilizer cycle by measuring biological change due to growth of any spores remaining within such indicator material.

10. The method of claim 9, including
    directing radiation of a wavelength, selected in the visible light spectrum, through such sealed encapsulating barrier of a test ampoule, and
    measuring such visible change indication of thermal sterilization effectiveness by measuring for absorption of such visible light wavelength, as a result of color change response of such indicator material within such sealed test ampoule, so as to produce an indication of sterilization effectiveness which is free of any requirement for spore growth time-delay after exposure to such thermal sterilizer cycle.

11. The method of claim 10, including the step of providing spectrophotometer means for
    (i) measuring such color change in such indicator material by absorbance measurements for at least two selected wavelengths within such visible light spectrum, and
    (ii) interrelating such absorbance measurements to obtain a quantitative indication of microbial sterility.

* * * * *